United States Patent
Wenzel et al.

(10) Patent No.: US 8,423,118 B2
(45) Date of Patent: Apr. 16, 2013

(54) MODEL-BASED DIFFERENTIAL DIAGNOSIS OF DEMENTIA AND INTERACTIVE SETTING OF LEVEL OF SIGNIFICANCE

(75) Inventors: Fabian Wenzel, Hamburg (DE); Stewart Young, Hamburg (DE); Torjoern Vik, Hamburg (DE); Frank O. Thiele, Aachen (DE); Ralph Buchert, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 306 days.

(21) Appl. No.: 12/665,783

(22) PCT Filed: May 27, 2008

(86) PCT No.: PCT/IB2008/052081
§ 371 (c)(1),
(2), (4) Date: Dec. 21, 2009

(87) PCT Pub. No.: WO2008/155682
PCT Pub. Date: Dec. 24, 2008

(65) Prior Publication Data
US 2010/0179415 A1    Jul. 15, 2010

Related U.S. Application Data

(60) Provisional application No. 60/945,405, filed on Jun. 21, 2007.

(51) Int. Cl.
*A61B 5/00* (2006.01)
(52) U.S. Cl.
USPC .......... 600/407; 600/408; 600/410; 600/425; 600/436; 382/128; 382/131

(58) Field of Classification Search .......... 600/407–408, 600/410–423, 425, 436; 382/128, 131
See application file for complete search history.

(56) References Cited

U.S. PATENT DOCUMENTS

| 5,109,868 A | 5/1992 | Smith et al. |
| 5,182,793 A | 1/1993 | Alexander et al. |

(Continued)

FOREIGN PATENT DOCUMENTS

| JP | 2005237441 A | 9/2005 |
| WO | 2005121796 A2 | 12/2005 |

OTHER PUBLICATIONS

Jelinek, H., et al.; A comparison of machine learning approaches for the automated classification of dementia; 2002; Lecture Notes in Artificial Intelligence; vol. 2557; abstract.

(Continued)

*Primary Examiner* — Ruth S Smith

(57) ABSTRACT

When detecting and classifying hypo-metabolic regions in the brain to facilitate dementia diagnosis, a patient's brain scan image, generated using an FDG-PET scan, is compared to a plurality of hypo-metabolic region patterns in brain scan images associated with a plurality of types of dementia. In a fully automated mode, the patient's scan is compared to all scans stored in a knowledge base, and a type of dementia associated with a most likely match is output to a user along with a highlighted image of the patient' s brain. In a semi-automated mode, a user specifies two or more types of dementia, and the patient's scan is compared to scans typical of the specified types. Diagnosis information including respective likelihoods for each type is then output to the user. Additionally, the user can adjust a threshold significance level to increase or decrease a number of voxels that are included in hypo-metabolic regions highlighted in the patient' brain scan image.

18 Claims, 8 Drawing Sheets

U.S. PATENT DOCUMENTS

| | | | |
|---|---|---|---|
| 5,408,996 A * | 4/1995 | Salb | 600/317 |
| 5,873,823 A | 2/1999 | Eidelberg et al. | |
| 6,430,430 B1 | 8/2002 | Gosche | |
| 6,558,324 B1 * | 5/2003 | Von Behren et al. | 600/440 |
| 7,627,156 B2 * | 12/2009 | Margolis et al. | 382/128 |
| 7,860,288 B2 * | 12/2010 | Bernhardt et al. | 382/128 |
| 2005/0010445 A1 | 1/2005 | Krishnan et al. | |
| 2005/0215889 A1 | 9/2005 | Patterson, II | |
| 2005/0244036 A1 | 11/2005 | Rusinek et al. | |
| 2005/0273007 A1 | 12/2005 | Burbar | |
| 2006/0023924 A1 * | 2/2006 | Asbeck et al. | 382/128 |
| 2006/0120584 A1 | 6/2006 | Hillman | |
| 2006/0155188 A1 * | 7/2006 | Walczak et al. | 600/421 |
| 2007/0036402 A1 | 2/2007 | Cahill et al. | |
| 2007/0260141 A1 * | 11/2007 | Margolis et al. | 600/437 |
| 2008/0051652 A1 * | 2/2008 | Ichioka et al. | 600/437 |

OTHER PUBLICATIONS

Mito, Y., et al.; Brain 3D-SSP SPECT analysis in dementia with Lewy bodies, Parkinson's disease with and without dementia, and Alzheimer's disease; 2005; Clinical Neurology and Neurosurgery; 107(5)396-403.

Sayeed, A., et al.; Diagnostic Features of Alzheimer's Disease Extracted from FDG PET Images; 2001; Engineering in Medicine and Biology Society; vol. 3:2770-2773.

Zhang, L., et al.; Machine Learning for Clinical Diagnosis from Functional Magnetic Resonance Imaging; 2005; IEEE Computer Society Conf. on Computer Vision and Pattern Recognition; vol. 1:1211-1217.

Zhuang, Z., et al.; Sprodice: a Diagnosis Support Program for the Interpretation of Brain CT Images; 1990; Transactions of the Institute of Electronics, Information and Communication Engineers D-II; vol. J73D-II; No. 11:1887-1896.

* cited by examiner

MODEL-BASED DIFFERENTIAL DIAGNOSIS OF DEMENTIA AND INTERACTIVE SETTING OF LEVEL OF SIGNIFICANCE

CROSS REFERENCE TO RELATED APPLICATIONS

This application claims the benefit of U.S. provisional application Ser. No. 60/945,405 filed Jun. 21, 2007, which is incorporated herein by reference.

The present application finds particular utility in positron emission tomography (PET) scanners in medical applications for diagnosing dementia. However, it will be appreciated that the described technique(s) may also find application in other types of scanning systems and/or other medical applications.

Early detection of Alzheimer's disease and differentiation from other types of dementia is an important aim in today's medical research due to an expected increase of patient numbers in response to current demographic trends. Current neurological tests such as the minimal mental state examination (MMSE) may help identify and grade different neurological diseases. However, clinical diagnosis per se is often uncertain and clinical assessment requires multiple examinations and laboratory tests over time. Thus, imaging has become an important part in the diagnosis of dementia.

PET imaging is able to show metabolic functionality of the brain when being used with corresponding tracers. For example, when used with an 18F-2-fluoro-deoxy-D-glucose (F18-FDG) tracer, PET images reveal hypo-metabolic regions in the brain as regions consisting of voxels with decreased intensity. Recent studies show that PET technology is promising for the early detection of dementia. According to another example, DaTSCAN can be used in clinical practice for differentiating between Alzheimer's disease and Lewy-Body disease.

Current software systems for the analysis of brain scans compute a statistical map indicating, for every voxel, statistically significant deviations from normal. Nowadays, these maps are examined by an expert, who visually classifies them into different types of dementia, such as Alzheimer's disease, Lewy-body disease, fronto-temporal disease, or healthy if the statistical map does not show severe patterns indicating hypo-metabolism. First approaches for automated discrimination between two types of dementia have been proposed, but are not used yet in clinical practice.

Thus, there is an unmet need in the art for systems and methods that facilitate overcoming the deficiencies noted above.

In accordance with one aspect, a system for automated differential diagnosis of dementia, includes a knowledge base (12) that comprises a plurality of brain scan images exhibiting typical patterns of a plurality of types and degrees of dementia and one or more healthy brain scan images, a processor (14) that receives information related to a patient's brain scan image and compares a patient's brain scan image to the brain scan images in the knowledge base (12), and a user interface (18) to which dementia diagnosis information is output for user review.

In accordance with another aspect, a method of automatically diagnosing dementia in a patient includes performing dimension reduction to generate feature vectors for a statistical mapping of a scanned image of a the patient's brain, weighting the feature vectors to indicate a relative ability of individual vectors to differentiate between types of dementia, and classifying the weighted features as corresponding to one or more of the plurality of types of dementia.

One advantage is that dementia diagnosis is automated, thereby mitigating opportunity for human error.

Another advantage resides in distinguishing between multiple types of dementia in a single pass.

Another advantage resides in an adjustable significance threshold level that facilitates early detection of dementia.

Another advantage resides in performing reproducible, quantitative analysis, in contrast to human analysis.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
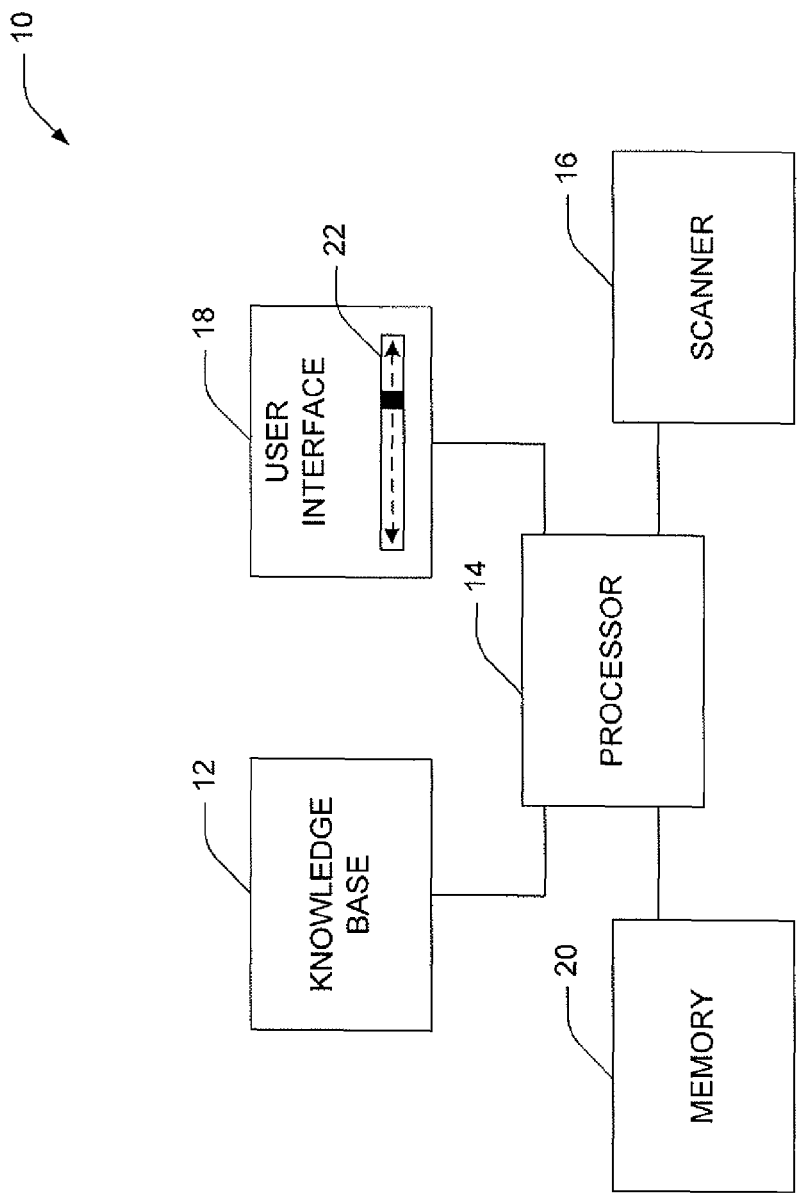
FIG. 1 illustrates a system for automated, model-based differential diagnosis of dementia by analysis of spatially normalized FDG-PET images.

FIG. 1 illustrates a system 10 for automated, model-based differential diagnosis of dementia by analysis of spatially normalized FDG-PET images. The system is based on a knowledge base 12, containing models for each of a plurality of types and/or degrees of dementia as well as the healthy brain, and has two operation modes. In the first, images are analyzed with respect to all models in the knowledge base. In the second, the user defines a subset of models in order to improve accuracy for a specific differential diagnosis task. In either mode, the system facilitates detecting whether a patient has dementia, and if so, what type(s) of dementia are present and to what degree or stage the dementia has progressed.

The system comprises the knowledge base 12, including a plurality of characteristic dementia scans that are used to train a processor 14 and/or one or more classifiers to facilitate analysis of a patient's brain scan image, as well as one or more healthy brain scans. The characteristic dementia scans can be, for example, statistical maps of brain scans, spatially normalized or otherwise preprocessed scans, etc. In one embodiment, the knowledge base comprises post-processed normalized scans (e.g., 34 in FIG. 2). The processor 14 is coupled to a scanner 16, such as a PET scanner or other suitable scanner (e.g., fMRI, etc.), which generates an image of a patient's brain for comparison to the characteristic images. Alternatively, the processor can be connected with a database that stores images generated by the scanner for later diagnosis. As different patterns of hypo-metabolic areas are specifically indicative of particular forms of dementia, PET imaging is useful for differential diagnosis, which facilitates different types of dementia being treated using different therapies and/or different medication.

The processor executes one or more comparison algorithms and outputs the patient's image, comparison information, diagnosis information regarding one or more likely types of dementia, and the like, to a user interface 18. The user interface 18 additionally includes a slider bar 22 that permits a user to interactively adjust a significance level (e.g. the acceptable rate of false positives) for detecting pathological change in patients.

Comparison algorithms, classifiers, classifier training algorithms and any other suitable data is stored in a memory 20 coupled to the processor 14. The memory 20 can be volatile or non-volatile memory, and is of a type suitable to the various functions described herein, as will be appreciated by those of skill.

According to an example, when a patient is injected with an FDG tracer (or other suitable tracer for discriminating between a subset of specific dementia types, etc.), and PET images of the patient are taken by the scanner, patients with dementia have hypo-metabolic regions (e.g., areas exhibiting reduced brain activity) of the brain, which appear on the PET images, with different types of dementia affecting different regions of the brain. Although some affected regions can overlap between different types of dementia, each type of dementia has a characteristic pattern of hypo-metabolic regions. Thus, during a learning phase, the processor evaluates the characteristic dementia scans in the knowledge base and determines respective characteristic patterns of hypo-metabolic areas associated with the different types of dementia.

During a diagnosing phase, an FDG-PET scan of the patient is performed, and the resultant hypo-metabolic map is compared to the characteristic maps for various types of dementia. In a semi-automatic mode, an operator specifies two or more types of dementia for comparison, and the system 10 determines which type is more likely. In a fully-automatic mode, the system compares the patient's map with the entire knowledge base of known dementia maps and proposes a diagnosis. Optionally, next-best diagnoses can be performed as well. Once the processor has identified all of the regions that are characteristically less active in hypo-metabolic maps, it combines all of the voxels within each region and determines a single indicator of inactivity for each region. Each of the several regions are weighted in accordance with their ability to differentiate among or between dementia patterns, and are combined. The processor then performs a statistical analysis to determine the likelihood that the hypo-metabolic map to be diagnosed is the result of each of two or more types of dementia.

Automated support for the task of discriminating between classes is desirable for a number of reasons. The interpretation of PET data requires considerable expertise, in particular for discrimination between subtly different patterns such as those in Alzheimer's disease (AD) and Lewy-body disease (LBD) patients. For experts, confirming a diagnosis is considerably less time-consuming than generating a diagnosis.

Accordingly, a computer-aided decision (CAD) system yielding objective and quantitative diagnostic information can provide a uniform standard of diagnosis independent of the available expertise, and thus contribute to the adoption of PET imaging beyond elite institutions, towards general practice.

According to another example, the system uses the knowledge base 12, containing previously diagnosed images (e.g. FDG-PET images, images using other tracers or other techniques like functional magnetic resonance imaging (fMRI)), along with the images' respective diagnoses. In one embodiment, different tracers are employed to assist in dementia pattern differentiation. The image and diagnosis data is organized into classes: one class for each type of dementia and an additional class for images not containing pathological findings (e.g., "healthy brain"). A user can configure and extend the knowledge base by providing classified training data. The following paragraphs describe the system for an FDG-PET scan of a patient, although other tracers and imaging techniques are covered by this invention. The system may operate in the two modes discussed above, described here in greater detail.

In the fully-automatic mode, differential diagnosis using the complete knowledge base can be performed. In this case, an FDG-PET image is analyzed with respect to all possible classes. The image is then assigned to the class with the highest likelihood. In the semi-automatic mode, differential diagnosis is performed with respect to a specific discriminative task defined by the user. For example, the user may want the system to perform the differential diagnosis with respect to two specific types of dementia: AD vs. LBD. In this case, only parts of the knowledge base (e.g., the classes for Alzheimer's disease and Lewy-Body disease) are used, providing more specific results.

The system is equipped with means to switch between the two operating modes (e.g. by clicking on buttons in or on the user interface 18, selecting a menu entry, etc.). For the semi-automatic operating mode, the system is equipped with means to let the user set up specific discrimination tasks (e.g. by offering buttons in/on the user interface so that the user can select the set of classes for which classification is to be performed, etc.). Automated differential diagnoses of a registered FDG-PET scan result in scores that can be interpreted as likelihoods or significance values for each class. Scores are presented to the user using soft or hard classification schemes.

Under a soft classification scheme, for each class, the corresponding score is presented to the user (e.g. "0% normal, 80% Alzheimer's disease, 20% Lewy-Body disease). Under a hard classification scheme, the class having the highest score is presented to the user (e.g. "Normal" if the scores have been computed as "90% normal, 10% Alzheimer's disease," etc.) Automated classification techniques may require a dimensionality reduction of the input data (in this case the image data). Examples include region-based analysis, where an atlas is used to define functional areas of the brain, and stereotactic surface projection. The processor can perform such data reduction and tailor it to the specific classification task, as selected by the user. The dependency between the classifier and the data reduction increases the efficiency of the selected classifier.

According to another example, the system employs a combination of two pattern recognition techniques. The first technique aims at reducing the amount of data used for classification ("dimension reduction"); whereas, the second performs soft classification. As a prior step, the set of training images is stored to the knowledge base 12, depending on the operation mode.

Dimension reduction is performed to determine a feature vector. All voxels V in an image belonging to a specific region R(i) are combined to a feature F(i) using a weight volume W, such that:

$$F(i) = \sum_{V \in R(i)} V(x, y, z) * W(x, y, z)$$

Regions R(i) may obtained by a predefined atlas of anatomical structures. In other embodiments, the atlas is an atlas of functional regions, a pre-defined atlas of disease-characteristic regions, an atlas of other previously-computed regions, or the like. As an alternative, a specific atlas targeted at the proposed system may be obtained by the following workflow. For instance, a set of discriminating volumes B(i) is computed by the processor using the training images of the knowledge base by partial least squares analysis. The processor then modifies discriminating volumes B(i) by replacing negative voxels with their respective absolute values. Modified discriminating B(i) volumes are combined into a volume C by addition, which is then segmented to obtain a set of regions R(i) for dimension reduction. As regions R(i) depend on the set of training images, they adapt to the task the user has chosen (e.g., operation mode, set of classes).

The weight volume W can be obtained using any of a number of different alternatives, including applying a constant weight, using weights obtained by voxel values of volume C (e.g., via region mean or more sophisticated modeling of the image), etc.

Once dimension reduction is complete, classification is performed by the processor to determine a score for each class. Feature vectors determined as described above are computed for all training images as well. A support vector machine (SVM) or other statistical or non-statistical classifiers may be applied for discrimination using the feature vector. It will be appreciated that all portions of the above-described technique(s) and algorithms that employ only training images may be computed off-line and incorporated in the knowledge base in order to reduce computation time.

Diagnosis information can be used as input for planning a course of treatment. Additionally or alternatively, the systems and/or methods set forth herein can be used to follow-up or monitor treatment status, to alter or adjust treatment(s), etc. According to an example, patient scans can be analyzed to glean information regarding similar dementia patterns and treatments (e.g., effectiveness of treatments at different stages, etc.). For instance, patients that have a common type of dementia can be scanned during treatment, and their scans can be analyzed to compare treatment effectiveness.

Figure 2:
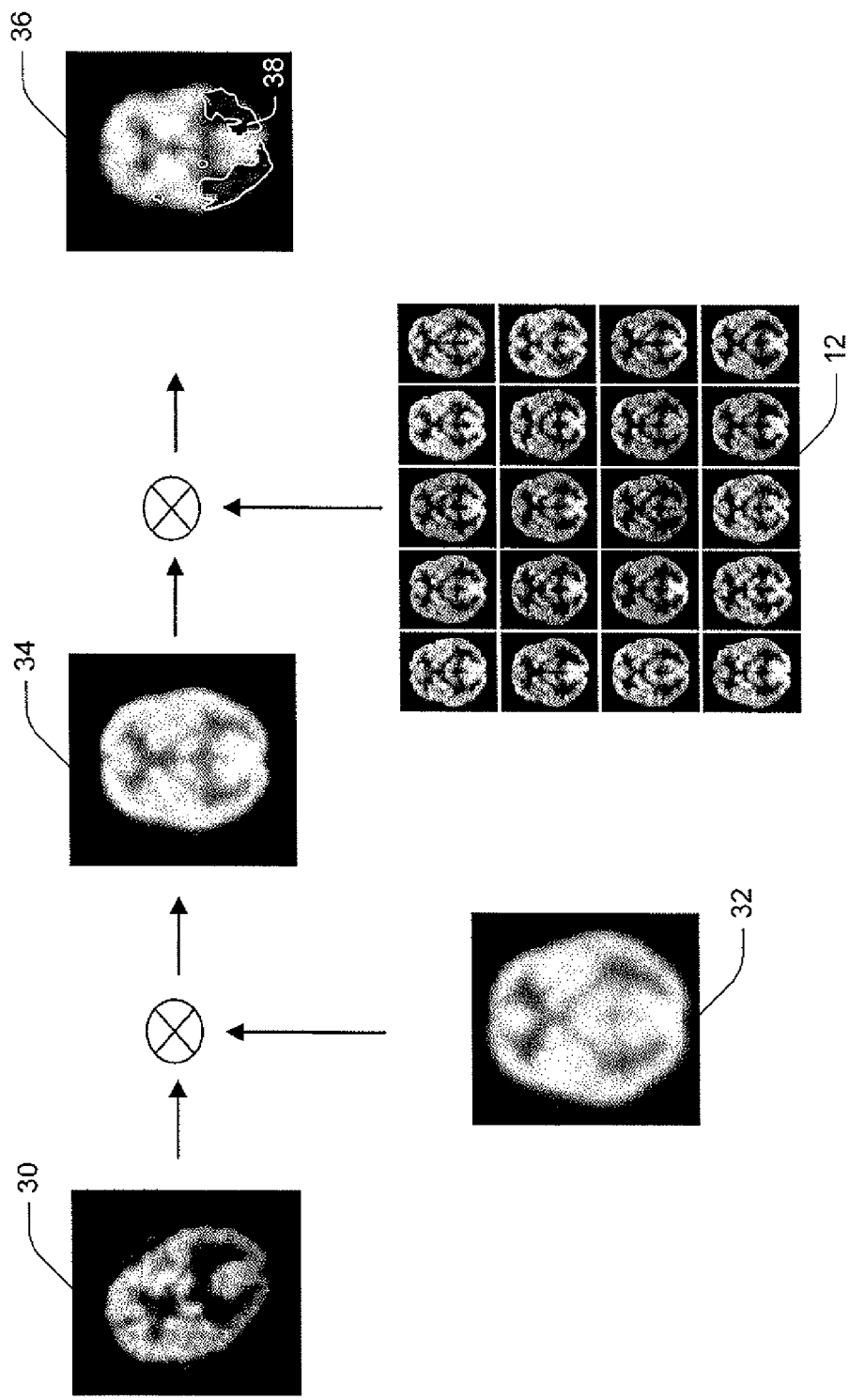
FIG. 2 shows a statistical map of a PET scan image of a patient's brain, which can be interactively manipulated by a user.

FIG. 2 shows a statistical map of a PET scan image of a patient's brain, which can be interactively manipulated by a user. For instance, an image 30 of a patient's brain is generated using a PET scanner, an fMRI scanner, or the like. The image is compared and/or adapted to a template brain model 32 to generate a spatially normalized patient brain image 34. The normalized image is then compared to "normal" brain images in the knowledge base 12, and a statistical map 36 of the patient's brain is generated, with statistically significant hypo-metabolic regions 38 highlighted.

Statistical brain mapping of FDG-PET brain images is a tool in clinical diagnosis of dementia patients. Diagnosis can be based, for instance, on pattern classification of typical dementia patterns in the statistical maps as described above. In accordance with one or more embodiments described herein, a user continuously adapts a threshold that corresponds to the significance level of the displayed statistical map using, for example, the slider bar 22 described with regard to FIG. 1. It will be appreciated that other means for adjusting significance can be employed in conjunction with the systems and/or methods described herein, such as a dial or keypad, and that means for adjusting significance levels can be digitally displayed on the user interface or hardware-based means (e.g., a physical knob, slider bar, etc.).

Statistical brain mapping can be used in clinical analysis of FDG-PET brain images, such as for diagnosis of Alzheimer's disease. In statistical brain mapping, the brain image of a patient is statistically compared to a control collective of brain images. This comparison is performed voxel-by-voxel. To do so, the following steps are performed: spatial ("stereo-tactical") normalization of patient image to brain template, computation of statistics (t-statistics or z-score), i.e. one scalar number per voxel, and display of (clusters of) those voxels that have a statistical value above a given threshold ("statistical map"). This threshold is intended to correspond to a level of significance, such as an acceptable rate of false positives. Voxels with a statistical value above the threshold are thus considered to be significantly different as compared to the control collective.

Common software tools to perform voxel-wise statistical brain mapping include Neurostat and statistical parametric mapping (SPM). With SPM, the desired level of significance for detecting pathological change in patients has to be specified before analysis. Then, the corresponding statistical map of voxels with statistically significant change is computed and displayed. Moreover, with SPM and Neurostat, z-scores above a significance threshold can be displayed voxel-wise. With these tools, the level of significance (e.g., the acceptable rate of false positives) for detecting pathological change in patients has to be specified before-hand, and the corresponding statistical map is displayed.

To determine the threshold that corresponds to a given level of significance, complicated mathematics are involved in the NeuroStat and SPM techniques, including approximations and reliance on some assumptions that may not be fulfilled. Therefore, the conventionally determined threshold is to some extent not well-defined. However, the diagnosis of dementia, as described herein, need not be based on the number of voxels that are significantly different from the control group at a given significance level. Rather, the diagnosis can be based on typical patterns of change in the patient image as compared to the control group. To better assess these patterns in a given patient, it is beneficial to assess the statistically significant changes at different thresholds. The slider bar 22 permits a user to evaluate a number of thresholds for a single analysis, rather than requiring a new analysis has to be performed for each threshold. That is, by continuously changing the threshold, the clinician can assess the existence of typical dementia patterns much more easily and quickly. The emergence of characteristic patterns with hypo-metabolic maps at very low thresholds can lead to earlier diagnosis and treatment.

According to an embodiment, the z- or t-statistics of a patient image with regard to a control collective is calculated using SPM or NeuroStat techniques. The statistical map 36 is then displayed at some initial threshold level of significance as usual, but in addition, interactive slide bar allows the user to interactively vary the threshold without having to rerun the analysis. The displayed statistical map can be, for instance, 30 two-dimensional brain slides with 128×128 pixels. These can be adapted to the varying threshold in real time. The same is true for the standard representation of the statistical map as projection of a brain surface.

Figure 3:
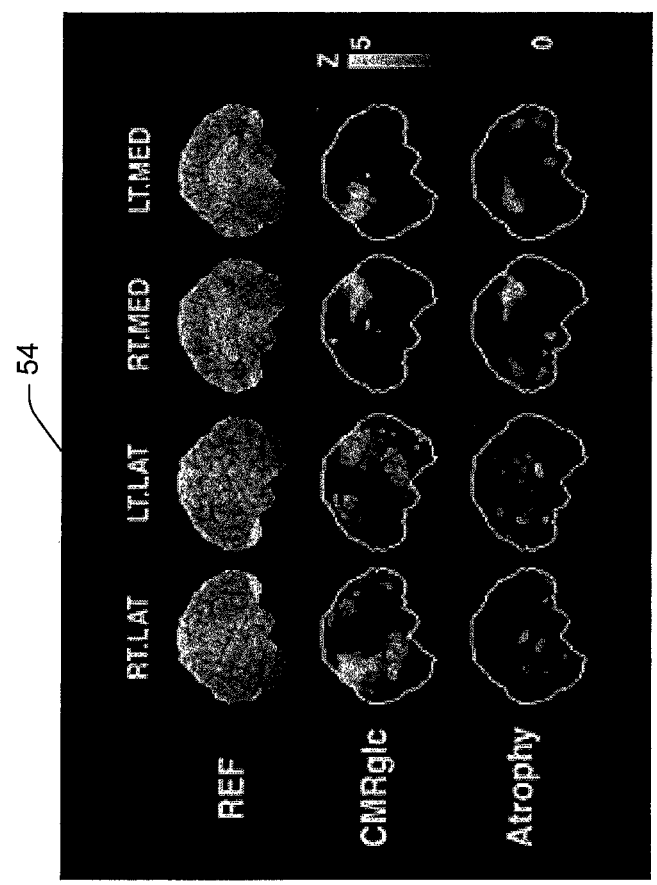
FIG. 3 is an illustration of screenshots of brain scans and overlaid parameter maps showing visualizations of hypo-metabolic voxels, obtained by two software systems used in academic clinical practice.
Figure 3:
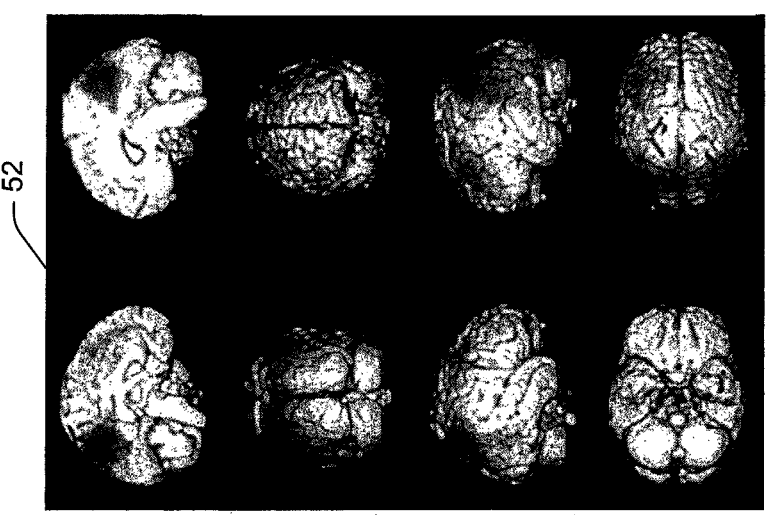

FIG. 3 is an illustration of screenshots of brain scans and overlaid parameter maps showing visualizations of hypo-metabolic voxels, obtained by two software systems used in academic clinical practice. A first screenshot 52 shows a plurality of views of a patient's brain with the hypo-metabolic regions shaded, as generated using an SPM technique. A second screenshot 54 shows a plurality of views of the patient's brain as generated using a NeuroStat technique.

Using computer-aided analysis of PET scans, other kinds of parameter data for individual voxels or regions in the brain can be obtained. In particular, parameter maps need not be limited to describe significant deviations from normal but may also indicate likelihood for their causes, such as a specific type of dementia (e.g. Alzheimer's disease, etc.). They may also be relevant for brain areas of voxels that have been tested to show abnormal intensity, but that do not relate to typical patterns of dementia.

Figure 4:
FIG. 4 is an illustration of a visualization of indicators for specific types of dementia. Other visualization types may be considered as well (e.g., contours, 3D views etc.), in accordance with various embodiments.

FIG. 4 is an illustration of a visualization of indicators for specific types of dementia. Other visualization types may be considered as well (e.g., 3D views, etc.), in accordance with various embodiments. The highlighted areas are obtained automatically by a prior automated analysis of the PET data, and/or by including other images such as MR images or additional information from a patient's medical record. In contrast to merely marking voxels or areas in the brain that are significantly different from normal, this embodiment uses a component of a computer-aided system for the differential diagnosis of dementia by highlighting regions that are indicative of a specific type of dementia. Parameter maps that indicate significance for specific types of dementia may be obtained by a variety of numerical analysis and pattern recognition techniques given a PET brain scan of the patient to be examined, a knowledge base, or other information, such as MR images of the same patient or data from medical records.

According to the figure, a number of Alzheimer's disease hypo-metabolic regions 60 are highlighted using a first color. A number of Lewy-Body disease hypo-metabolic regions 62 are highlighted using a second color. Finally, a number of unclassified hypo-metabolic regions 64 (e.g., hypo-metabolic regions detected in locations not associated with a particular form of dementia) are highlighted in a third color). Color-coding is performed by a processor or the like after comparison of a patient's brain scan map to the knowledge base. The color-coded highlighting scheme aids a technician in determining a correlation between a patient's map and one or more typical dementia maps.

Figure 5:
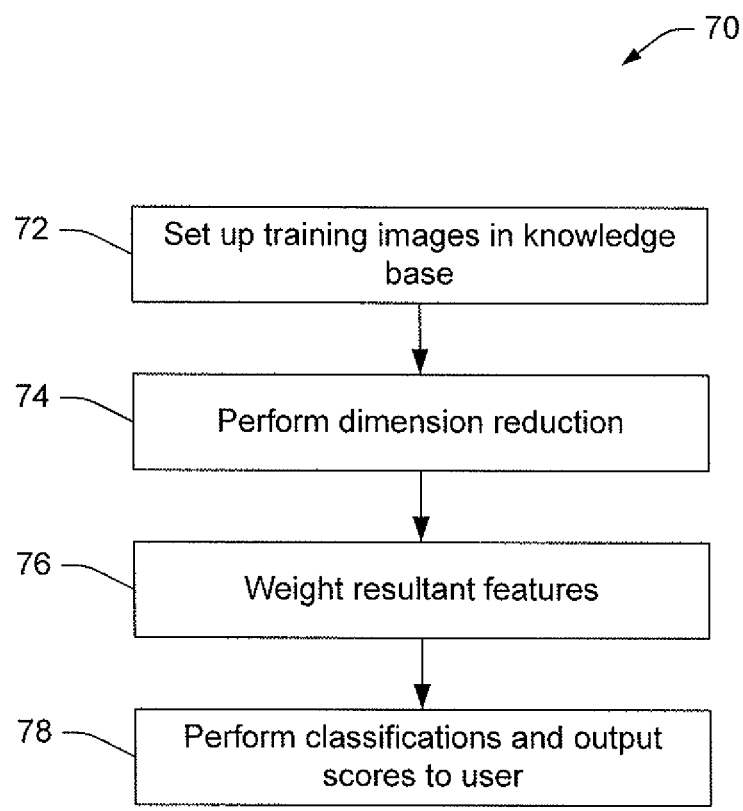
FIG. 5 illustrates a method of performing differential diagnosis of various types and/or degrees of dementia in a patient using an automatic or semi-automatic diagnosis technique, in accordance with various aspects.

FIG. 5 illustrates a method 70 of performing differential diagnosis of various types and/or degrees of dementia in a patient using an automatic or semi-automatic diagnosis technique, in accordance with various aspects. At 72, a knowledge base is pre-constructed and includes a number of brain scan images corresponding to different types of dementia, as well as "normal" brain scans not exhibiting dementia-related hypo-metabolic regions. At 74, a dimension reduction algorithm is executed to generate a feature vector. For example, all voxels V in an image belonging to a specific region R(i) of the patient's brain map are combined to a feature F(i). Regions R(i) can be obtained from a predefined atlas of anatomical structures, an atlas of functional regions, a pre-defined atlas of disease-characteristic regions, an atlas of other previously-computed regions, or the like. Alternatively, a specific atlas can be generated using the method of FIG. 6, described below.

At 76, the resultant features are weighted, such that $$F(i) = \sum_{V \in R(i)} V(x, y, z) * W(x, y, z).$$

The weight volume W can be a constant weight, can be obtained from voxel values of an aggregate volume C (described below), etc. At 78, the feature vectors are classified and scored, and such scores are output to a user. For instance, a support vector machine or other statistical or non-statistical classifier can be used to distinguish between feature vectors. Output of the scores in a fully automatic mode, a proposed diagnosis is output as a function of the type of dementia most closely resembling the patient's hypo-metabolic map. In a semi automatic mode, the scores for two or more types of dementia selected by the user are output, wherein the scores describe a similarity between the patient's hypo-metabolic map and the respective dementia type maps.

Figure 6:
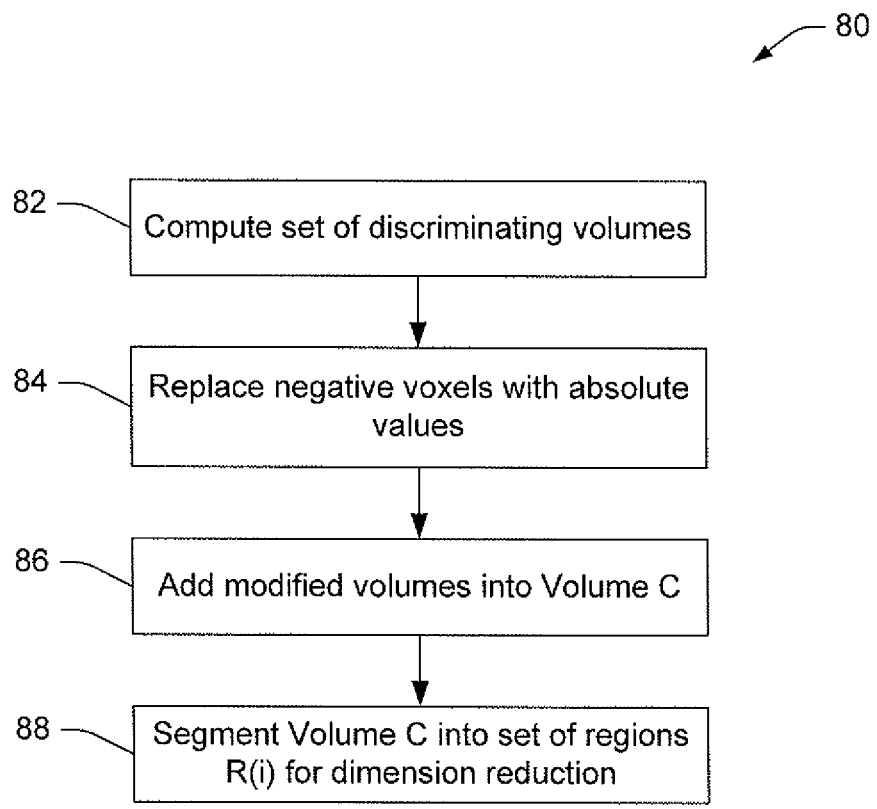
FIG. 6 illustrates a method for generating an atlas or comprehensive map for use in generating weighted features when performing dimension reduction.

FIG. 6 illustrates a method 80 for generating an atlas or comprehensive map for use in generate weighted features when performing dimension reduction. For instance, at 82, a set of discriminating volumes B(i) is computed using the training images by, for example, partial least squares analysis. In another embodiment, a group-based statistical comparison technique is employed. At 84, discriminating volumes B(i) are modified by replacing negative voxels with their absolute values. At 86, modified discriminating B(i) volumes are combined into a volume C by addition. At 88, volume C is segmented to obtain a set of regions R(i) for dimension reduction. As regions R(i) depend on the set of training images, they adapt to the task the user has chosen (operation mode, set of classes, etc.).

Figure 7:
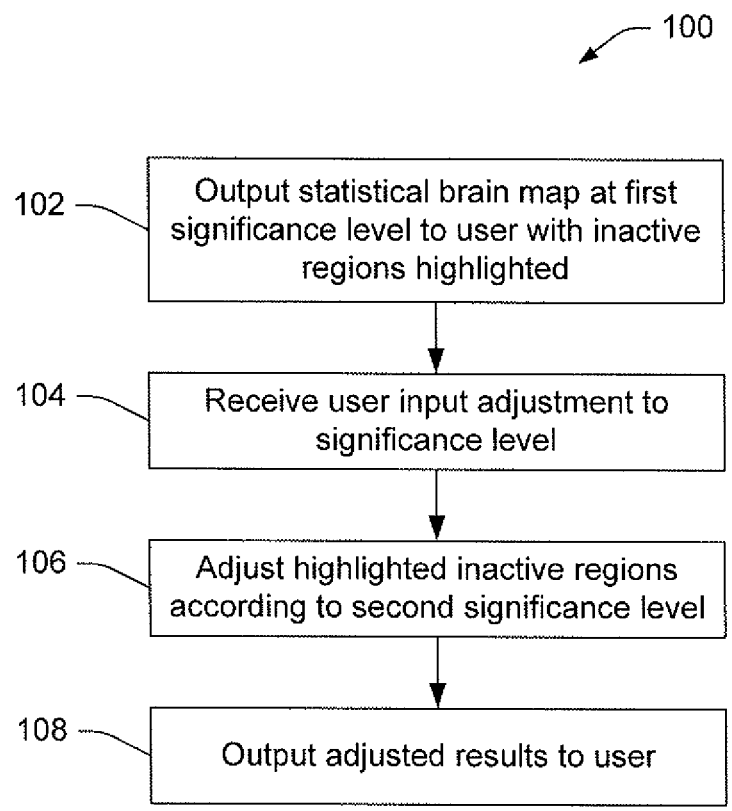
FIG. 7 illustrates a method of interactively adjusting statistical significance for a patient's hypo-metabolic brain map after a single analysis pass.

FIG. 7 illustrates a method 100 of interactively adjusting statistical significance for a patient's hypo-metabolic brain map after a single analysis pass. At 102, a statistical brain map of the patient (e.g. 36 in FIG. 2) is output at a first significance level to a user on a user interface (e.g., a computer monitor or the like) with hypo-metabolic regions highlighted. According to one embodiment, the scan is an FDG-PET scan, although other scanning techniques can be employed (e.g., fMRI, etc.). At 104, user input is received to adjust the statistical significance level (e.g., the acceptable rate of false positives, etc.) in the display of the statistical map, via a slide bar, dial, or the like. At 106, the hypo-metabolic regions are adjusted (e.g., by a processor or the like) to include or exclude voxels according to the new significance level entered by the user. At 108, the adjusted results are output to the user. In this manner, the user can dynamically alter the highlighted hypo-metabolic regions in the statistical map as a function of a level of significance without having to re-start the analysis of the PET scan image at the new significance level. Accordingly, the user can more readily detect typical dementia patterns.

According to an example, the first significance level can be a default level or can be selected by the user, e.g. twice the normal variation ($z=2$), so that regions or voxels in the PET image of the brain having values that are at least two standard variations of the normal variation less than the normal average activity in those voxels, are deemed statistically significant and included in the highlighted hypo-metabolic regions. In this example, regions or voxels that exhibit an activity level that are 1.5 standard deviations below normal are not included in the representation of the hypo-metabolic region(s). Using the adjustable significance level technique described herein, a user can reduce the significance level to, for instance, 1.5 standard deviations below normal, 1 standard deviation below normal, etc., in order to evaluate whether a significant portion of the brain is exhibiting below-normal function in that range. If a significant increase in size of the highlighted hypo-metabolic region results due to the slight decrease in significance level, then the user may conclude that the patient is in the early stages of dementia, and the specific type of dementia may further be deduced using the automatic diagnosis systems or techniques described above. For instance, the specific areas in which the hypo-metabolic regions are located can be compared to the knowledge base of typical dementia patterns to deduce the type of dementia suffered by the patient.

In another embodiment, a series of decreasing significance levels can be displayed to the user (e.g., at pre-defined significance intervals or the like). For instance, the series of significance levels can be presented to the user in a loop format, such that the display cycles through several significance levels in order to exhibit a trend. This information can be employed by a user in generating a diagnosis, a treatment plan, (e.g., growth patterns with decreasing significance versus database results for the same, etc.) etc.

Figure 8:
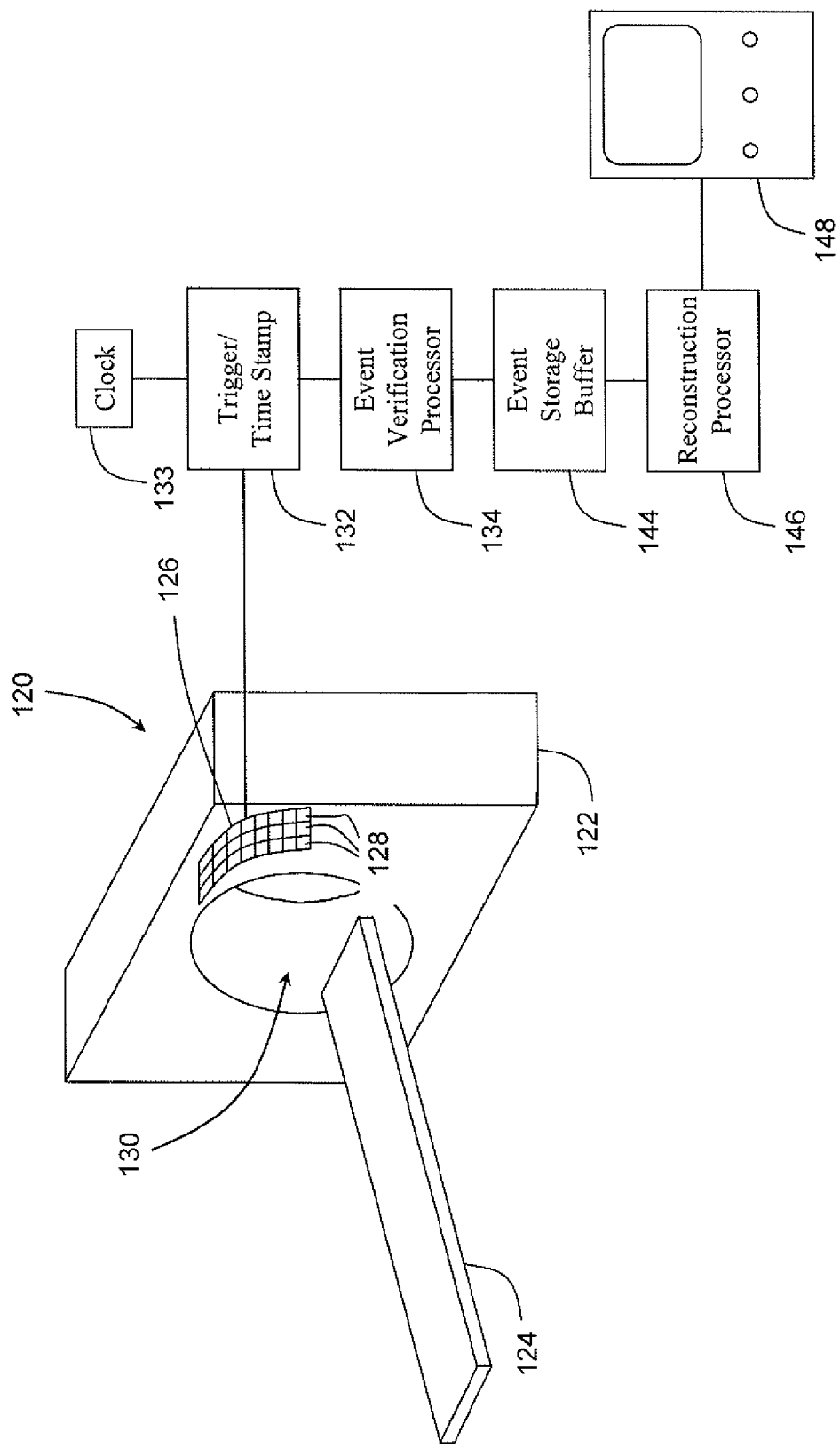
FIG. 8 illustrates a diagnostic imaging device such as may be employed in conjunction with one or more of the systems and/or methods described herein.

FIG. 8 illustrates a diagnostic imaging device 120 such as may be employed in conjunction with one or more of the systems and/or methods described herein. The diagnostic imaging device 120 includes a housing 122 and a subject support 124. Enclosed within the housing 122 is a detector array 126. The detector array 126 includes a plurality of individual detector elements 128. The array 126 is arranged so that detector elements 128 are distributed evenly about an imaging region 130. The detector array 126 can be a ring of detectors 128, multiple rings, or discrete flat panels disposed opposing each other. Whatever the actual placement or arrangement of the detectors 128, it is preferable to arrange the detectors such that each detector has a plurality of counterpart detectors across the imaging region to facilitate coincidence detection. In positron emission tomography (PET), pairs of gamma rays are produced by a positron annihilation event in the imaging region and travel in opposite directions. These gamma rays are detected as pairs, with a slight delay (on the order of nanoseconds) between detections if one gamma ray travels farther to reach a detector than the other.

Before the PET scan commences, a subject is injected with a radiopharmaceutical. The radiopharmaceutical contains a radioactive element coupled to a tag molecule. The tag molecule is associated with the region to be imaged, and tends to gather there through normal body processes. For example, rapidly multiplying cancer cells tend to expend abnormally high amounts of energy duplicating themselves. So, the radiopharmaceutical can be linked to a molecule, such as glucose that a cell typically metabolizes to create energy, gather in such regions and appear as "hot spots" in the image. Other techniques monitor tagged molecules flowing in the circulatory system.

For PET imaging the selected radioisotope emits positrons. The positron can only move a very short distance (on the order of nanometers) before it is annihilated in an annihilation reaction that creates two oppositely directed gamma rays. The pair of gamma rays travel in opposite directions at the speed of light striking an opposing pair of detectors.

When a gamma ray strikes the detector array 126, a time signal is generated from a leading edge of the resultant electrical pulse. A triggering processor 132 monitors each detector 128 for an energy spike, e.g., integrated area under the pulse, characteristic of the energy of each received gamma ray. The triggering processor 132 checks a clock 133 and stamps each detected gamma ray with a time of leading edge receipt stamp. The time stamp is first used by an event verification processor 134 to determine which gamma rays form a pair that defines a line of response (LOR). Because gamma rays travel at the speed of light, if detected gamma rays arrive more than several nanoseconds apart, they probably were not generated by the same annihilation event and are discarded. Timing is especially important in TOF-PET, as the minute difference in substantially simultaneous events can be used to further localize the annihilation event along the LOR. As computer processor clock speeds become faster, the higher the accuracy with which an event can be localized along its LOR. In a SPECT camera, the LOR or trajectory for each detected gamma ray is determined by collimation.

LORs are stored in an event storage buffer 144, and a reconstruction processor 146 reconstructs the LORs into an image representation of the subject using filtered backprojection or other appropriate reconstruction algorithm. The reconstruction can then be displayed for a user on a display device 148, forwarded to the processor 14, printed, saved for later use, and the like.

Having thus described the preferred embodiment, the invention is now claimed to be:

1. A system for automated differential diagnosis of dementia, including:
   a knowledge base that comprises a plurality of brain scan images exhibiting patterns of a plurality of types and degrees of dementia and one or more healthy brain scan images;
   a processor configured to:
      receive information related to a patient's brain scan image having at least one hypometabolic region;
      generate feature vectors for a statistical map of the patient's brain scan image, the statistical map showing one or more statistically significant hypo-metabolic regions;
      weight the feature vectors to indicate a relative ability of individual vectors to differentiate between types of dementia;
      compare the statistical map of the patient's brain scan image to the brain scan images in the knowledge base; and
      identify a brain scan image in the knowledge base having a hypo-metabolic region pattern similar to the statistical map of the patient's brain scan image; and
   a user interface to which dementia diagnosis information is output for user review;
   wherein the diagnosis information includes an image of the patient's brain scan image with highlighted hypo-metabolic regions;
   wherein the highlighting is color-coded to indicate a type of dementia;
   wherein different colors correspond to different types of dementia.

2. The system according to claim 1, further including a scanner that scans the patient and generates the brain scan image.

3. The system according to claim 2, wherein the scanner is one of:
   a positron emission tomography (PET) scanner, and the brain scan image is generated using a 18F-2-fluoro-deoxy-D-glucose (F18-FDG) tracer; and
   a functional magnetic resonance imaging (fMRI) scanner.

4. The system according to claim 1, wherein the dementia diagnosis information is determined at least in part as a function of a correlation between locations of hypo-metabolic regions in the statistical map of the patient's brain scan image to locations of hypo-metabolic regions in the brain scan images in the knowledge base.

5. The system according to claim 1, wherein the processor automatically compares a hypo-metabolic region pattern in the statistical map of the patient's brain scan image to hypo-metabolic region patterns in brain scan images for types of dementia represented by brain scan images in the knowledge base, and outputs a diagnosis comprising a most likely type of dementia causing the hypo-metabolic region pattern in the statistical map of the patient's brain scan image.

6. The system according to claim 1, wherein the processor compares a hypo-metabolic region pattern in the statistical map of the patient's brain scan image to hypo-metabolic region patterns in brain scan images for two user-specified types of dementia represented by brain scan images in the knowledge base, and outputs dementia diagnosis information comprising a relative likelihood that each user-specified type of dementia is causing the hypo-metabolic region pattern in the statistical map of the patient's brain scan image.

7. The system according to claim 1, wherein the user interface includes a significance adjuster via which a significance threshold level is increased or decreased for the statistical map of the patient's brain scan image to decrease or increase a number of voxels that are included in the highlighted hypo-metabolic regions.

8. The system according to claim 1, wherein the processor is further configured to:
compute a set of discriminating volumes B(i) using images in the knowledge base by partial least squares analysis;
modify the discriminating volumes B(i) by replacing negative voxels with their respective absolute values;
combine the modified discriminating volumes B(i) into a volume C by addition;
segment the volume C to obtain a set of regions R(i) for dimension reduction;
perform dimension reduction on voxels V in an image belonging to a specific region R(i) to generate the feature vectors; and
classify the weighted feature vectors, and output results to the user interface as dementia diagnosis information for user review.

9. The system according to claim 1, wherein the processor is configured to:
generate the feature vectors for the statistical map of the patient's brain scan image by performing feature dimension reduction; and
classify the weighted feature vectors as corresponding to one or more of the plurality of types of dementia.

10. A method of automatically diagnosing dementia in a patient, including:
performing dimension reduction to generate feature vectors for a statistical map of a scanned image of the patient's brain;
weighting the feature vectors to indicate a relative ability of individual vectors to differentiate between a plurality of types of dementia;
classifying the weighted features as corresponding to one or more of the plurality of types of dementia; and
generating and outputting the statistical map of the patient's brain to a user, with hypo-metabolic regions highlighted, and providing diagnosis information to the user, the diagnostic information being based on a comparison of hypo-metabolic regions in the statistical map to known hypo-metabolic region patterns for the plurality of types of dementia;
wherein the highlighting is color-coded to indicate a type of dementia such that different colors correspond to different types of dementia.

11. The method according to claim 10, wherein classifying the weighted features includes comparing the weighted features to all brain scan images with hypo-metabolic region patterns associated with all types of dementia represented in a knowledge base, and wherein the diagnosis information includes a most likely type of dementia based on the comparison.

12. The method according to claim 10, wherein classifying the weighted features includes comparing the weighted features to brain scan images with hypo-metabolic region patterns associated with at least two user-specified types of dementia represented in a knowledge base, and wherein the diagnosis information includes a likelihood associated with each user-specified type of dementia based on the comparison.

13. The method according to claim 12, further including adjusting a significance threshold level of brain activity relative to a normal level of brain activity.

14. The method according to claim 13, further including using a slider bar control to adjust the significance threshold level.

15. The method according to claim 10, further including providing training images in a knowledge base, the training images including a plurality of brain scan images with hypo-metabolic region patterns associated with a plurality of types of dementia, wherein the training images are employed to train a classifier prior to classifying the weighted features as corresponding to one or more of the plurality of types of dementia.

16. A processor programmed to perform the method of claim 10.

17. An automatic dementia diagnosis apparatus, including:
a knowledge base that stores a plurality of hypo-metabolic region patterns indicative of a plurality of types of dementia;
a scanner that scans a patient's brain to generate a scan image thereof for detection of at least one hypometabolic region;
a processor configured to:
perform dimension reduction to generate feature vectors for a statistical map of the patient's brain scan image, the statistical map showing one or more statistically significant hypo-metabolic regions;
weight the feature vectors to indicate a relative ability of individual vectors to differentiate between types of dementia; and
classify the weighted features as corresponding to one or more of the plurality of types of dementia;
compare the statistical map of the patient's brain scan image to the plurality of hypo-metabolic region patterns;
determine a likelihood that one or more of the patterns matches a pattern of hypo-metabolic regions in the statistical map of the patient's brain scan image; and
identify a brain scan image in the knowledge base having a hypo-metabolic region pattern similar to the statistical map of the patient's brain scan image; and
a user interface that presents diagnostic results to a user, including highlighted hypo-metabolic regions in the patient's brain scan image;
wherein the highlighting is color-coded to indicate a type of dementia;
wherein different highlighting colors correspond to different types of dementia.

18. The apparatus according to claim 17, wherein the processor is further configured to adjust a significance threshold level for the diagnostic results to increase or decrease a number of voxels included in the highlighted hypo-metabolic regions in the statistical map of the patient's brain scan image.

* * * * *